(12) United States Patent
Han et al.

(10) Patent No.: US 10,959,637 B2
(45) Date of Patent: Mar. 30, 2021

(54) AUTOMATIC DETECTION/CLASSIFICATION OF ECG CABLE INTERCHANGE FOR DIFFERENT ECG LEAD SYSTEMS

(71) Applicant: KONINKLIJKE PHILIPS N.V., Eindhoven (NL)

(72) Inventors: Chengzong Han, Andover, MA (US); Richard Gregg, Westford, MA (US); Saeed Babaeizadeh, Arlington, MA (US)

(73) Assignee: Koninklijke Philips N.V., Eindhoven (NL)

( * ) Notice: Subject to any disclaimer, the term of this patent is extended or adjusted under 35 U.S.C. 154(b) by 465 days.

(21) Appl. No.: 15/563,136

(22) PCT Filed: Mar. 31, 2016

(86) PCT No.: PCT/EP2016/057143
§ 371 (c)(1),
(2) Date: Sep. 29, 2017

(87) PCT Pub. No.: WO2016/156534
PCT Pub. Date: Oct. 6, 2016

(65) Prior Publication Data
US 2018/0092568 A1 Apr. 5, 2018

Related U.S. Application Data

(60) Provisional application No. 62/140,878, filed on Mar. 31, 2015.

(51) Int. Cl.
A61B 5/04 (2006.01)
A61B 5/0428 (2006.01)
(Continued)

(52) U.S. Cl.
CPC ........ *A61B 5/04286* (2013.01); *A61B 5/0424* (2013.01); *A61B 5/0428* (2013.01);
(Continued)

(58) Field of Classification Search
CPC . A61B 5/04286; A61B 5/0456; A61B 5/7221; A61B 5/0424; A61B 2562/222;
(Continued)

(56) References Cited

U.S. PATENT DOCUMENTS 6,282,440 B1 * 8/2001 Brodnick ........... A61B 5/04011
600/512
6,721,591 B2 4/2004 Kojima et al.
2007/0232946 A1 * 10/2007 Feild .................... A61B 5/0424
600/509

FOREIGN PATENT DOCUMENTS

CN 103908244 A 7/2014

OTHER PUBLICATIONS

Han, C. et al., "Automatic detection of ECG cable interchange by analyzing both morphology and interlead relations", Journal of Electrocardiology., vol. 47, No. 6, Nov. 1, 2014, pp. 781-787. (Year: 2014).*

(Continued)

Primary Examiner — Rex R Holmes

(57) ABSTRACT

An ECG controller for an ECG device is connectable to a base ECG lead system (e.g., a 12-lead system) whereby the ECG controller implements an ECG waveform morphology based and ECG lead redundancy based detection and classification of any cable interchange (e.g., a limb cable interchange or a precordial cable interchange) between the ECG controller and the base ECG lead system. Alternatively, the ECG controller is further connectable to a sub-base ECG lead system (e.g., a limb only-lead system or a limited precordial-lead system) whereby the ECG controller implements an ECG waveform morphology based detection and (Continued)

classification of any cable interchange (e.g., a limb cable interchange or a precordial cable interchange) between the electrode interface and the sub-base ECG lead system.

20 Claims, 11 Drawing Sheets

(51) Int. Cl.
  *A61B 5/00* (2006.01)
  *A61B 5/0424* (2006.01)
  *A61B 5/0456* (2006.01)
(52) U.S. Cl.
  CPC .......... *A61B 5/0456* (2013.01); *A61B 5/7221* (2013.01); *A61B 2560/0276* (2013.01); *A61B 2562/222* (2013.01); *A61B 2562/226* (2013.01); *A61B 2562/227* (2013.01)
(58) Field of Classification Search
  CPC ........ A61B 2562/226; A61B 2562/227; A61B 2560/0276; A61B 5/0428
  See application file for complete search history.

(56) References Cited

OTHER PUBLICATIONS

Xia, H. et al. (Automatic detection of ECG electrode misplacement: a tale of two algorithms', Physiological Measurement, Institute of Physics Publishing, Brlstoi, GB, voi. 33, No. 9, Aug. 17, 2012, pp. 1549-1561) (Year: 2012).*

Han, C. et al., Automatic detection of ECG lead-wire interchange for conventional and Mason-Likar lead systems:, Computing in Cardiology 2013, N/A, Sep. 7, 2014, pp. 145-148.

Han, C. et al., "Automatic detection of ECG cable interchange by analyzing both morphology and interlead relations", Journal of Electrocardiology., vol. 47, No, 6, Nov. 1, 2014, pp. 781-787.

Xia, H. et al., Automatic detection of ECG electrode misplacement: a tale of two algorithms', Physiological Measurement, Institute of Physics Publishing, Bristol, GB, vol. 33, No. 9, Aug. 17, 2012, pp. 1549-1561.

Batchvarov, V.N. et al., "Incorrect electrode cable connection during electrocardiographic recording", Europace, vol. 9, No. 11, Oct. 3, 2007, pp. 1081-1090, GB.

Kors, J. et al., "Accurate Automatic Detection of Electrode Interchange in the Electrocardiogram", American Journal of Cardiology, Cahners Publishing Co., Newton, MA, vol. 88, No. 4, Aug. 15, 2001, pp. 396-399.

\* cited by examiner

AUTOMATIC DETECTION/CLASSIFICATION OF ECG CABLE INTERCHANGE FOR DIFFERENT ECG LEAD SYSTEMS

This application is a national stage application under 35 U.S.C. § 371 of International Application No. PCT/EP2016/057143 filed on Mar. 31, 2016 and published in the English language on Oct. 6, 2016 as International Publication No. WO2016/156534, which claims priority to U.S. Patent Application No. 62/140,878 filed on Mar. 31, 2015, the entire disclosures of which are incorporated herein by reference.

FIELD OF THE INVENTION

The present invention generally relates to an automatic detection of misconnections of electrocardiograph leadwires to the electrodes fastened to the patient's body (i.e., cable interchange). The present invention specifically relates to a comprehensive automatic detection and classification of electrocardiograph cable interchange for different ECG lead systems.

BACKGROUND OF THE INVENTION

Generally, accurate placement of electrocardiogram ("ECG") electrodes is vital for both a standard lead system (e.g., a conventional 12-lead system) and a non-standard lead system (e.g., a Mason-Likar reduced lead system). Sometimes the ECG electrodes are placed on the correct anatomical locations, but one or more electrode lead-wires are erroneously connecting ECG electrode(s) to wrong terminal(s) at an ECG device (e.g., a right arm electrode is mistakenly connected to the left arm lead-wire of the ECG device). An erroneous connection of ECG device lead-wire to the wrong patient electrode is known as "cable interchange" in the art, and a cable interchange typically generates an erroneous waveform during any ECG reconstruction and/or an erroneous diagnosis during an ECG analysis.

More particularly, forty (40) million ECGs are recorded annually in the United States. The standard 12-lead ECG is obtained using ten (10) electrodes, including four (4) limb electrodes and six (6) precordial electrodes. The four (4) limb electrodes include right arm (RA), left arm (LA), right leg (RL) and left leg (LL), while the six (6) precordial electrodes (V1-V6) are placed on anatomically referenced landmarks on the anterior chest. Electrode placement is considered one of the most important factors that determine ECG signal quality, and electrode misplacement tend to produce incorrect ECG abnormalities and thus generate erroneous diagnostic reports. ECG cable interchange is one of the most common electrode placement errors. Consequently, the American Heart Association recommends including cable interchange detection algorithms in all ECG devices.

To this end, researchers have proposed several criteria and methods to detect ECG cable interchange. In terms of automatic detection algorithms, most methods fall into one of two (2) categories. The first category of automatic detection algorithms involves morphology-based methods which extract a set of measurements from P, QRS, and T-waves and use these measurements to derive detection criteria. The second category of automatic detection algorithms implements redundancy-based methods which use redundant information contained in the eight (8) independent leads of a standard 12-lead system. Such methods use the transformation or reconstruction of ECGs from the original lead system to an approximation, and cable interchange is detected by comparing the original ECGs with transformed or reconstructed ECGs.

More particularly, existing methods for detecting ECG cable interchange were designed for resting diagnostic ECG devices which use standard 12-lead system with limb electrodes placed at standard positions. However, for a wide range of ECG devices, other non-standard lead systems are often used. For example, in monitoring or exercise ECG devices, the Mason-Likar lead system is often used. In the Mason-Likar lead system, modified limb electrode positions are often used whereby the arm electrodes are placed at the infraclavicular fossae and the LL electrode is placed on the left lower abdomen. As another example, in telemetry ECG devices, reduced-lead systems (e.g., lead system recording limb lead only or limb lead plus limited precordial leads) are often used.

As with the standard 12-lead system, a detection of ECG cable interchange is necessary for ECG devices with non-standard lead systems. For example, in the monitoring/exercise ECG device, the accurate placement of ECG electrode is important during ST-segment monitoring. As such, detection of an ECG cable interchange could help prevent false alarms during ST-segment monitoring. While some ST-segment deviation is normal, the amount and polarity depends on the electrode position. In that way, the same magnitude and polarity of ST deviation may be normal in one combination of electrodes, but abnormal in another set of electrodes. Additionally, in the reduced-lead systems, a 12-lead ECG may be reconstructed from the reduced-lead recordings and a misconnection of lead-wires could generate erroneous 12-lead waveforms.

SUMMARY OF THE INVENTION

The present invention aims to address the above-mentioned limitations of existing methods for detecting ECG cable interchange by providing a comprehensive detection of ECG cable interchange for different ECG lead systems.

Generally, the present invention is premised on an ECG controller for an ECG device by coupling, integration or otherwise any structural relationship between the ECG controller and the ECG device that facilitates the ECG controller communicating a message to or from the ECG device indicating an absence or a presence of a cable interchange between the ECG controller and an ECG lead system.

For purposes of the present invention, the term "ECG device" broadly encompasses all stand-alone devices and multi-function systems incorporated devices for generating and displaying (i.e., monitoring) an ECG of a patient's heart including, but not limited to:

1. diagnostic ECG devices (e.g., PageWriter TC cardiographs, Efficia series of cardiograph);
 2. exercise ECG devices (e.g., ST80i stress testing system);
 3. ambulatory ECG devices (Holter monitor);
 4. bed-side monitoring ECG device (e.g., IntelliVue monitors, SureSigns monitors, and Goldway monitors);
 5. telemetry ECG device (e.g., IntelliVue MX40 monitor);
 6. and advanced life support products (e.g., HeartStart MRx and HeartStart XL defibrillators, and Efficia DFM100 defibrillator/monitor);
 7. ECG management system (e.g., IntelliSpace ECG management system).

The ECG controller may be connected to a base ECG lead system (e.g., a standard 12-lead system, a 15-lead system, a 16-lead system or a 18-lead system) whereby the ECG controller collectively implements an ECG waveform morphology based/ECG lead redundancy based detection and classification of any cable interchange between the ECG controller and the base ECG lead system.

Alternatively, the ECG controller may be connected to a sub-base lead system (e.g., a four (4) electrode lead wire system and a six (6) electrode lead wire system) whereby the ECG controller implements an ECG waveform morphology based detection and classification of any cable interchange between the ECG controller and the sub-base ECG lead system.

For purposes of the present invention, the term "base ECG lead system" broadly encompasses electrodes and cable lead-wires of an ECG lead system established for connection of electrodes on the patient's skin to the ECG device (electrocardiograph) lead-wires. The term "sub-base ECG lead system" broadly encompasses a subset of electrodes and cable lead-wires of a base ECG lead system.

For purposes of the present invention, the term "ECG controller" broadly encompasses all structural configurations of an application specific main board or an application specific integrated circuit housed within or linked to an ECG device for controlling an application of various inventive principles of the present invention as subsequently described herein. The structural configuration of the ECG controller may include, but is not limited to, processor(s), computer-usable/computer readable storage medium(s), an operating system, application module(s), peripheral device ECG controller(s), slot(s) and port(s).

For purposes of the present invention, the term "application module" broadly encompasses a component of the ECG controller consisting of an electronic circuit and/or an executable program (e.g., executable software and/firmware) for executing a specific application.

One form of the present invention is the ECG controller employing application modules in the form of an electrode interface, an ECG interpreter and a cable interchange classifier.

In operation, the electrode interface is in connection with either the base ECG lead system or the sub-base ECG lead system to receive ECG signals.

The ECG interpreter:
(1) generates an ECG waveform from the ECG signals; and
(2) extracts morphology feature(s) of the ECG waveform.

The cable interchange classifier:
(1) when the electrode interface is connected to the sub-base ECG lead system, detects and classifies any cable interchange between the electrode interface and the sub-base ECG lead system based on the morphology feature(s) of the ECG waveform;
(2) when the electrode interface is connected the base ECG lead system, generates redundancy feature(s) of the base ECG lead system, and
detects and classifies any cable interchange between the electrode interface and the base ECG lead system based on the morphology feature(s) of the ECG waveform and the redundancy feature(s) of the base ECG lead system.

For purposes of the present invention, terms of the art including, but not limited to, "ECG signals", "ECG waveform", "cable interchange", "morphology" and "redundancy", are to be interpreted as understood in the art of the present invention and as exemplary described herein.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

Figure 1A:
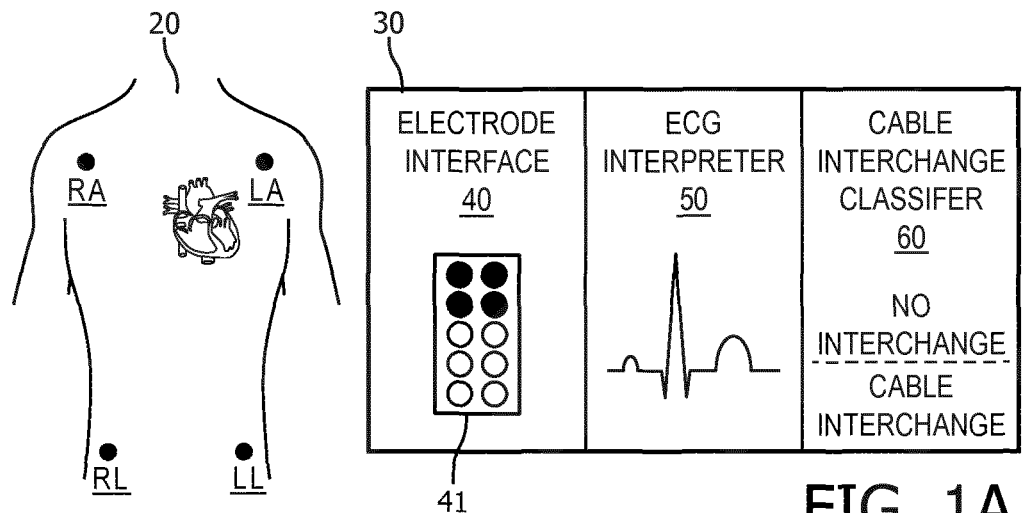
FIGS. 1A-1C illustrate block diagrams of exemplary embodiments of an ECG lead system/ECG controller connection in accordance with the inventive principles of the present invention.
Figure 1B:
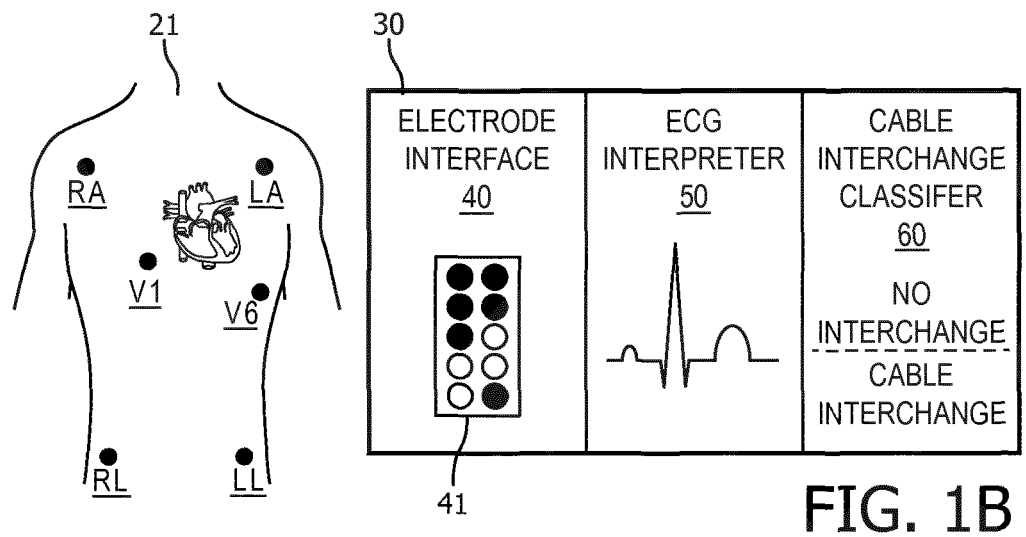
Figure 1C:
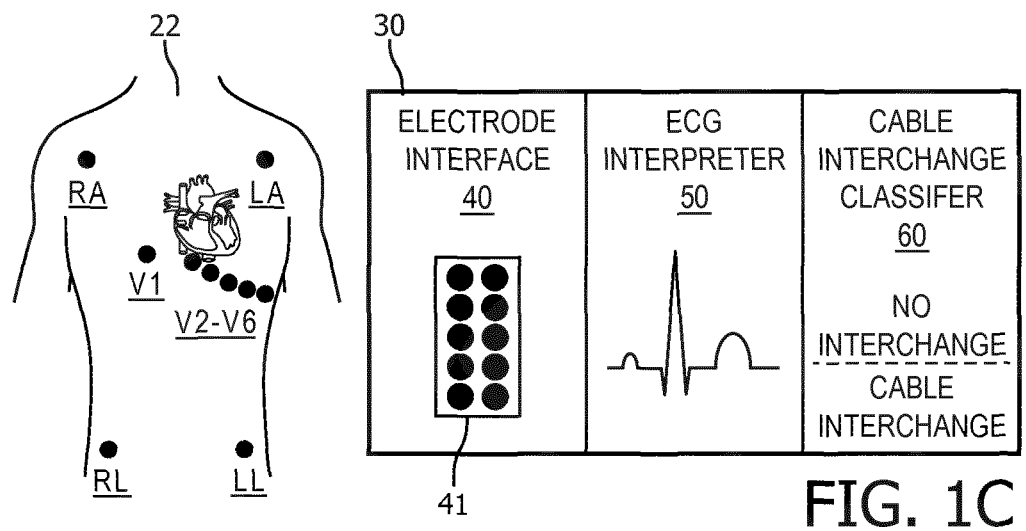

To facilitate an understanding of the present invention, the following description of FIGS. 1A-1C and FIG. 2 teaches basic inventive principles of a cable interchange method implemented by an ECG controller 30 connectable to a limb only-lead system 20 of FIG. 1A, a limited precordial-lead system 21 of FIG. 1B or a standard 12-lead system 22 of FIG. 1C. From this description, those having ordinary skill in the art will appreciate how to apply the inventive principles of the present invention for an ECG controller connectable to every type of ECG lead systems.

Generally, the present invention addresses any misconnection between an ECG electrode and a corresponding lead-wire within an ECG lead system as connected to a terminal of ECG controller 30, and any misconnection between a correct pairing of an ECG electrode/lead-wire and a corresponding terminal of ECG controller 30. Thus, the description herein of FIGS. 1A-1C are directed to both types of misconnections as encompassed by the phrasing of "a cable interchange between a terminal configuration of the ECG controller and one the ECG lead systems".

Referring to FIGS. 1A-1C, ECG controller 30 employs an electrode interface 40, an ECG interpreter 50 and a cable interchange classifier 60. Electrode interface 40 has a terminal configuration 41 for connection to either limb only-lead system 20, limited precordial-lead system 21 or standard 12-lead system 22 in accordance with the following Table 1:

TABLE 1

|  | COLUMN 1 | COLUMN 2 |
| --- | --- | --- |
| ROW 1 | RA electrode | LA electrode |
| ROW 2 | LL electrode | RL electrode |
| ROW 3 | V1 electrode | V2 electrode |
| ROW 4 | V3 electrode | V4 electrode |
| ROW 5 | V5 electrode | V6 electrode |

Referring to FIG. 1A, limb only lead-system 20 includes a proper anatomical placement of an RA electrode, a LA electrode, a LL electrode and a RL electrode as shown. A proper connection of limb-only lead-system 20 to terminal configuration 41 via a cable connector (not shown) is in accordance with the following Table 2:

TABLE 2

|  | COLUMN 1 | COLUMN 2 |
| --- | --- | --- |
| ROW 1 | RA electrode | LA electrode |
| ROW 2 | LL electrode | RL electrode |
| ROW 3 |  |  |
| ROW 4 |  |  |
| ROW 5 |  |  |

An example of a misconnection of limb only lead-system 20 to terminal configuration 41 via a cable connector (not shown for clarity) in the form of a LA-RA cable interchange is in accordance with the following Table 3:

TABLE 3

|  | COLUMN 1 | COLUMN 2 |
| --- | --- | --- |
| ROW 1 | LA electrode | RA electrode |
| ROW 2 | LL electrode | RL electrode |
| ROW 3 |  |  |
| ROW 4 |  |  |
| ROW 5 |  |  |

Those having ordinary skill in the art will appreciate additional examples of a misconnection of limb only lead-system 20 to terminal configuration 41 (i.e. additional possible cable interchanges).

Referring to FIG. 1B, limited precordial lead-system 21 includes a proper anatomical placement RA electrode, LA electrode, LL electrode, RL electrode, a precordial electrode V1 and a precordial electrode V6 as shown (note other combination pair of precordial electrodes may be utilized). A proper connection of limited precordial lead-system 21 to terminal configuration 41 via a cable connector (not shown for clarity) is in accordance with the following Table 4:

TABLE 4

|  | COLUMN 1 | COLUMN 2 |
| --- | --- | --- |
| ROW 1 | RA electrode | LA electrode |
| ROW 2 | LL electrode | RL electrode |
| ROW 3 | V1 electrode |  |
| ROW 4 |  |  |
| ROW 5 |  | V6 electrode |

An example of a misconnection of limited precordial lead-system 21 to terminal configuration 41 via a cable connector (not shown for clarity) in the form of a V1-V6 cable interchange is in accordance with the following Table 5:

TABLE 5

|  | COLUMN 1 | COLUMN 2 |
| --- | --- | --- |
| ROW 1 | RA electrode | LA electrode |
| ROW 2 | LL electrode | RL electrode |
| ROW 3 | V6 electrode |  |
| ROW 4 |  |  |
| ROW 5 |  | V1 electrode |

Those having ordinary skill in the art will appreciate additional examples of a misconnection of limited precordial lead-system 21 to terminal configuration 41 (i.e. additional possible cable interchanges).

Referring to FIG. 1C, standard 12-lead system 22 includes a proper anatomical placement RA electrode, LA electrode, LL electrode, RL electrode, precordial electrode V1, a precordial electrode V2, a precordial electrode V3, a precordial electrode V4, a precordial electrode V5, and precordial electrode V6 as shown. A proper connection of standard 12-lead system 22 to terminal configuration 41 via a cable connector (not shown for clarity) is in accordance with the following Table 6:

TABLE 6

|  | COLUMN 1 | COLUMN 2 |
| --- | --- | --- |
| ROW 1 | RA electrode | LA electrode |
| ROW 2 | LL electrode | RL electrode |
| ROW 3 | V1 electrode | V2 electrode |
| ROW 4 | V3 electrode | V4 electrode |
| ROW 5 | V5 electrode | V6 electrode |

An example of a misconnection of standard 12-lead system 22 to terminal configuration 41 via a cable connector (not shown) in the form of a LA-LL cable interchange is in accordance with the following Table 7:

TABLE 7

|  | COLUMN 1 | COLUMN 2 |
| --- | --- | --- |
| ROW 1 | RA electrode | LL electrode |
| ROW 2 | LA electrode | RL electrode |
| ROW 3 | V1 electrode | V2 electrode |
| ROW 4 | V3 electrode | V4 electrode |
| ROW 5 | V5 electrode | V6 electrode |

Those having ordinary skill in the art will appreciate additional examples of a misconnection of standard 12-lead system 22 to terminal configuration 41 (i.e. additional possible cable interchanges).

Figure 2:
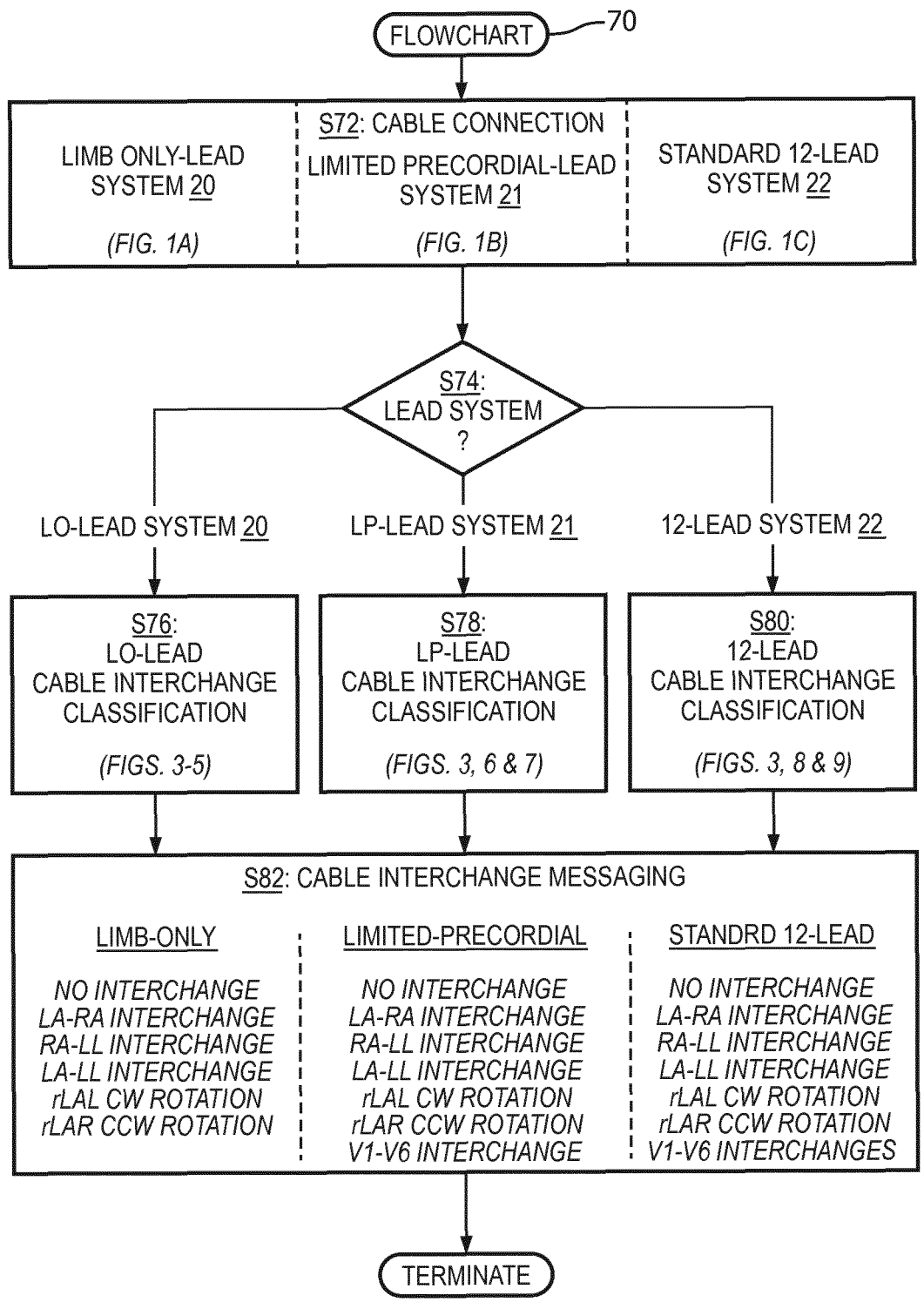
FIG. 2 illustrates a flowchart representative of an exemplary embodiment of a cable interchange management method in accordance with the inventive principles of the present invention.

Referring to FIGS. 1A-1C, upon connection of either lead system 20-22 to terminal configuration 41, ECG controller 30 executes a cable interchange management method of the present invention represented by a flowchart 70 of FIG. 2.

Additionally referring to FIG. 2, a stage S74 of flowchart 70 encompasses electrode interface 40 ascertaining a particular type of cable connection to terminal configuration 41 during a stage S72 of flowchart 70 based on a number of connected terminals to indicate a connection to limb only-lead system 20, limited precordial-lead system 21 or standard 12-lead system 22.

For a connection to limb only-lead system 20, electrode interface 40 provides incoming ECG signals to ECG interpreter 50 for a generation of an ECG waveform, and provides a codeword to cable interchange classifier 60 to indicate the system 20 connection whereby cable interchange classifier 60 executes an ECG waveform morphology based cable interchange classification of the connection to limb only-lead system 20 during a stage S76 of flowchart 70. The result is a cable interchange messaging by classifier 60 during a stage S82 of flowchart 70 consisting of:

1. No interchange (Table 2);
2. a LA-RA interchange (Table 3);
3. a RA-LL interchange;
4. a LA-LL interchange;
5. a rLAL CW rotation; or
6. a rLAR CC3 rotation.

For a connection to limited precordial-lead system 21, electrode interface 40 provides incoming ECG signals to ECG interpreter 50 for generation of the ECG waveform, and provides a codeword to cable interchange classifier 60 identifying the system 21 connection whereby cable interchange classifier 60 executes an ECG waveform morphology based cable interchange classification of the connection to limited precordial-lead system 21 during a stage S78 of flowchart 70. The result is a cable interchange messaging by classifier 60 during stage S82 consisting of:

1. No interchange (Table 4);
2. a LA-RA interchange;
3. a RA-LL interchange;
4. a LA-LL interchange;
5. a rLAL CW rotation;
6. a rLAR CC3 rotation; or
7 a V1-V6 precordial interchange (Table 5).

For a connection to standard 12-leady system 22, electrode interface 40 provides incoming ECG signals to ECG interpreter 50 for generation of the ECG waveform, and provides a codeword to cable interchange classifier 60 identifying the system 22 connection whereby cable interchange classifier 60 executes an ECG waveform morphology/lead redundancy based cable interchange classification of the connection to standard 12-lead system 22 during a stage S80 of flowchart 70. The result is a cable interchange messaging by classifier 60 during stage S82 consisting of:

1. No interchange (Table 6);
2. a LA-RA interchange;
3. a RA-LL interchange;
4. a LA-LL interchange (Table 7);
5. a rLAL CW rotation;
6. a rLAR CC3 rotation; or
7. any combination of V1-V6 precordial interchange.

Note, while not described as an example herein, the RL electrode in practice may be involved in a cable interchange and the present invention may be practiced to cover cable interchanges for all electrodes of an ECG lead system or a selected subset thereof.

Figure 3:
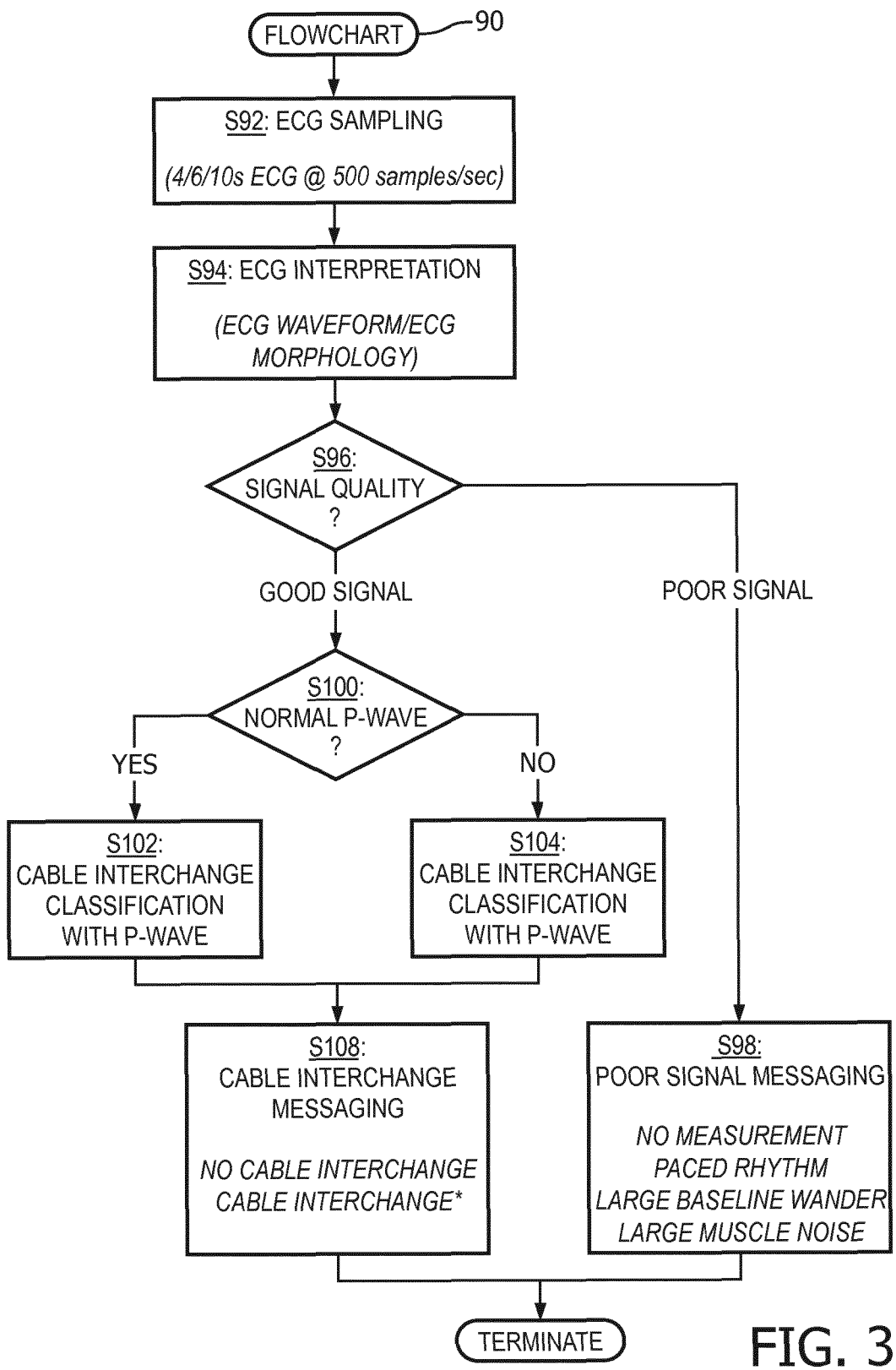
FIG. 3 illustrates a flowchart representative of an exemplary embodiment of a cable interchange detection/classification method in accordance with the inventive principles of the present invention.

Referring to FIG. 3, a flowchart 90 represents a cable interchange detection/classification method executed by ECG interpreter 50 and cable interchange classifier 60 during stage S76, stage S78 or stage S80 of flowchart 70 (FIG. 2) in dependence of the lead system connection.

A stage S92 of flowchart 90 encompasses ECG interpreter 50 sampling the incoming ECG signals (e.g., @ 500 samples/sec), and a stage S94 of flowchart 90 encompasses ECG interpreter 50 generating the ECG waveform.

In practice, ECG interpreter 50 may implement any known algorithm during stage S94 including, but not limited to, a Philips DXL ECG algorithm.

If the generated ECG waveform has a poor signal quality as ascertained by ECG interpreter 50 during a stage S96 of flowchart 90, then ECG interpreter 50 proceeds to communicate a descriptive poor signal message during a stage S98 of flowchart 90. A range of poor signal messages include, but are not limited to, "no measurement", "paced rhythm", "a large baseline wander" and "a large muscle noise".

If the generated ECG waveform has a good signal quality as ascertained by ECG interpreter 50 during stage S96, then ECG interpreter 50 proceeds to a stage S100 of flowchart 90 to ascertain if a P-wave of the generated ECG waveform is normal or abnormal. In practice, the P-wave of the ECG waveform may be considered normal when the ECG waveform has a consistent beat-to-beat PR interval, and does not show atrial fibrillation or atrial flutter. Otherwise, the P-wave of the ECG waveform may be considered abnormal when the ECG waveform has an inconsistent beat-to-beat PR interval or is showing atrial fibrillation or atrial flutter.

If the P-wave is normal, then ECG interpreter 50 and cable interchange classifier 60 proceed to a stage S102 of flowchart 90 to execute a cable interchange classification with P-wave morphology dependent upon the particular identified ECG lead system connection. Otherwise, if the P-wave is abnormal, then ECG interpreter 50 and cable interchange classifier 60 proceed to a stage S104 of flowchart 90 to execute a cable interchange classification without P-wave morphology dependent upon the particular identified ECG lead system connection.

Upon completion of either stage S102 or S104 for the appropriate lead system connection and P-wave normality decision, a stage S108 of flowchart 90 encompasses cable interchange classifier 60 generating the appropriate message as previously discussed herein for stage S82 of flowchart 70 (FIG. 2).

Stages S102 and S104 will now be described herein in the context of an identified ECG lead system connection.

Figure 4:
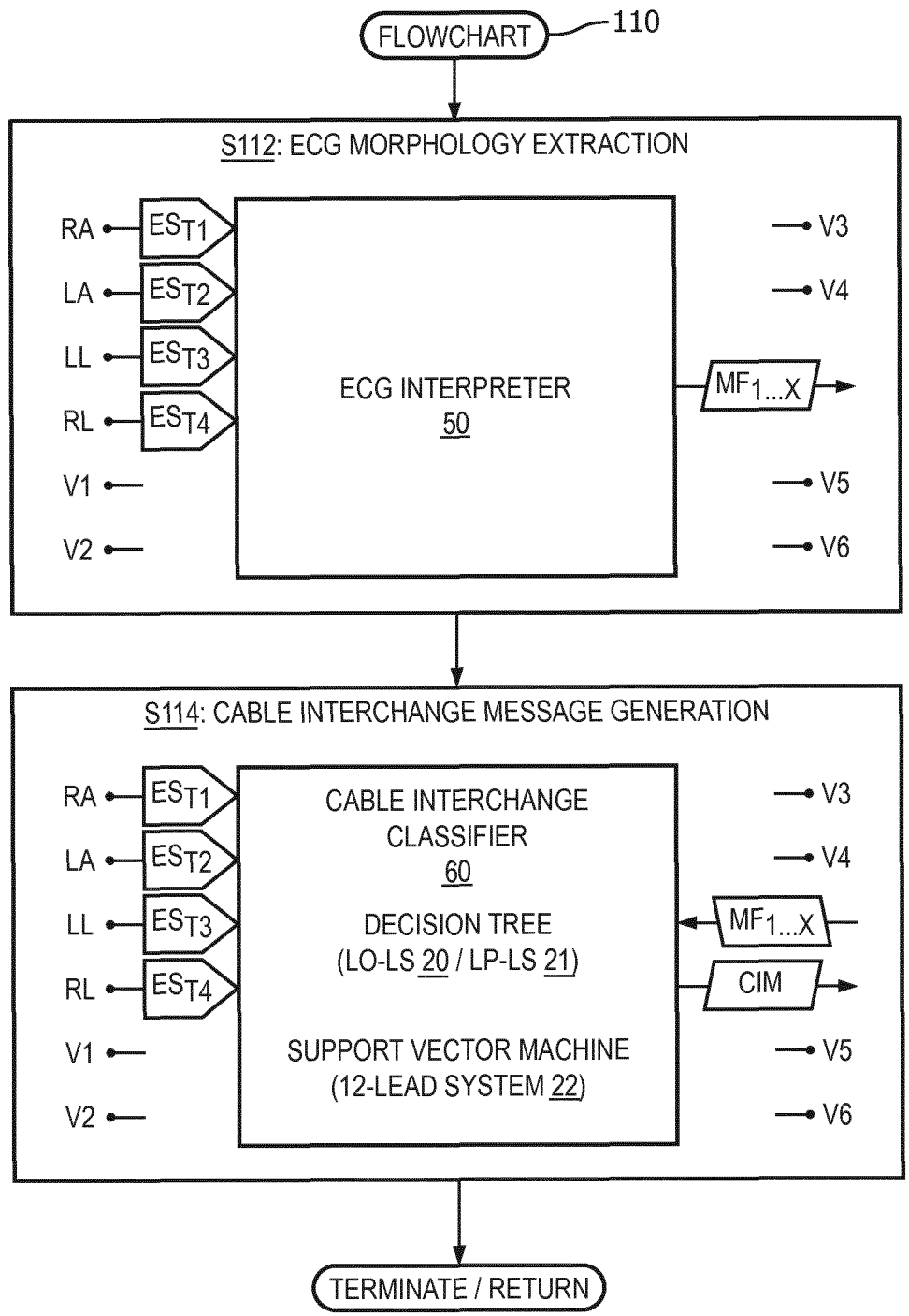
FIG. 4 illustrates a flowchart representative of a first exemplary embodiment of a morphology based detection/classification method in accordance with the inventive principles of the present invention.

Referring to FIG. 4, a flowchart 110 represents a cable interchange classification with P-wave and without P-wave for an identified connection to limb only-lead system 20.

A stage S112 of flowchart 110 encompasses ECG interpreter 50 extracting morphology features necessary for a cable interchange message generation during a stage S114 of flowchart 110. Specifically, stage S112 shows four (4) ECG signals $ES_{T1}$-$ES_{T4}$ being communicated to ECG interpreter 50 via terminals T1-T4 of terminal configuration 41 whereby ECG interpreter 50 extracts up to an X number of ECG morphology features MF, $X \geq 1$.

For a normal P-wave, ECG interpreter 50 extracts and provides ECG morphology features MF including frontal axis of P-wave and QRS-wave and clockwise vector loop rotation direction of P-wave and QRS to cable interchange classifier 60 for executing stage S114.

For an abnormal P-wave, ECG interpreter 50 extracts and provides ECG morphology features including frontal axis of QRS-wave, clockwise vector loop rotation direction of QRS-wave, and amplitudes of R-wave for lead I and lead II to cable interchange classifier 60 for executing stage S114.

Note stage S112 shows "no cable interchange" between limb only-lead system 20 and terminal configuration 41. Nonetheless, those having ordinary skill in the art will appreciate the various cable interchanges that may occur for limb only-lead system 20.

Cable interchange classifier 60 incorporates a decision tree algorithm for limb only-lead system 20, a decision tree algorithm for limited precordial-lead system 21 and a support vector machine for standard 12-lead system 22. For flowchart 110, cable interchange classifier 60 executes the decision tree algorithm for limb only-lead system 20 for detecting and classifying any cable interchange between system 20 and terminal configuration 41. The decision tree is dependent upon the extracted features and utilizes predictive measurements of each extracted morphology feature should be chosen to balance sensitivity versus specificity.

Figure 5:
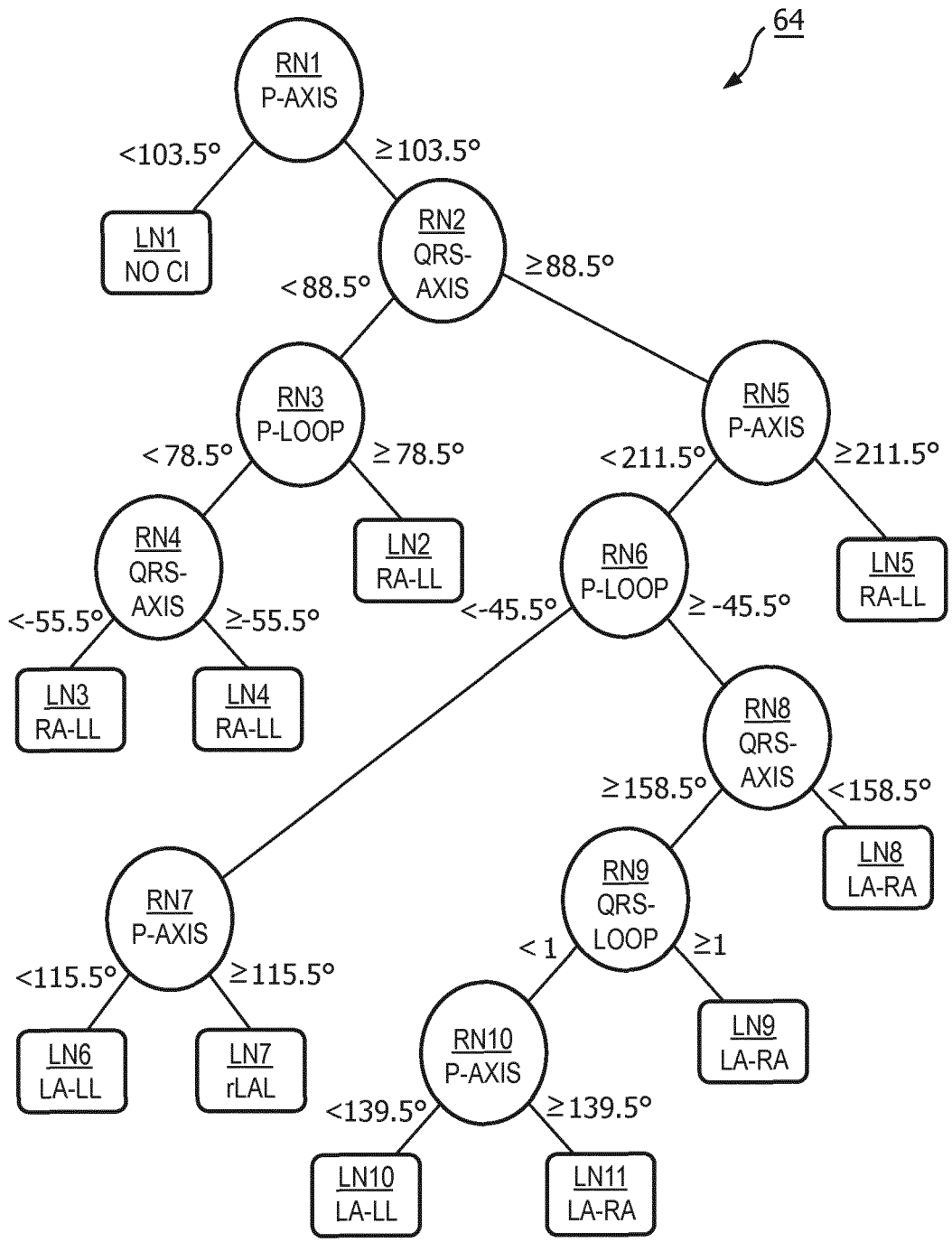
FIG. 5 illustrates a graphical diagram of a first exemplary embodiment of a decision tree in accordance with the inventive principles of the present invention.

Referring to FIG. 5, an exemplary decision tree 64 for a normal P-wave is shown. Decision tree 64 includes root nodes RN1-RN10 with each root node corresponding to a particular extracted ECG morphology feature. Decision tree 64 further includes leaf nodes LN1-LN11 with leaf node LN1 corresponding to no cable interchange and each leaf node LN2-LN11 corresponding to a particular cable interchange. The following Table 8 shows various message generations by cable interchange classifier 60 dependent upon specific measurements of extracted morphology features:

TABLE 8

|  | Measurement 1 | Measurement 2 | Measurement 3 |
|---|---|---|---|
| P-axis | 100° | 141° | 121° |
| P-loop [−100, 100] | 0 | 0 | 0 |
| QRS-axis | 116° | 116° | 85° |
| QRS-loop [−100, 100] | 0 | 0 | 0 |
| Cable Interchange Message | No CI | LA-RA | LA-LL |

From the description of FIG. 5, those having ordinary skill in the art will appreciate, (1) how to re-balance sensitivity versus specificity of decision tree 64 as needed, and (2) how to generate a decision tree for an abnormal P-wave and an alternative decision tree for normal P-wave, both including more or less or the same ECG morphology features as decision tree 64.

In practice, cable tree classifier 60 may utilize algorithms for limb only-lead system 20 other than a decision tree including, but not limited to, a linear regression, a logistic regression, a neural network, a naïve Bayes, and a discriminate analysis. Furthermore, any utilized algorithm may be used to solve a regression problem, which means in addition to detection of any cable interchange, each detection will be assigned a likelihood probability estimate.

Upon completion of stage S114, any cable interchange between limb only-lead system 20 and terminal configuration 41 has been accurately detected and classified, and classifier 60 provides a cable interchange message CIM.

Figure 6:
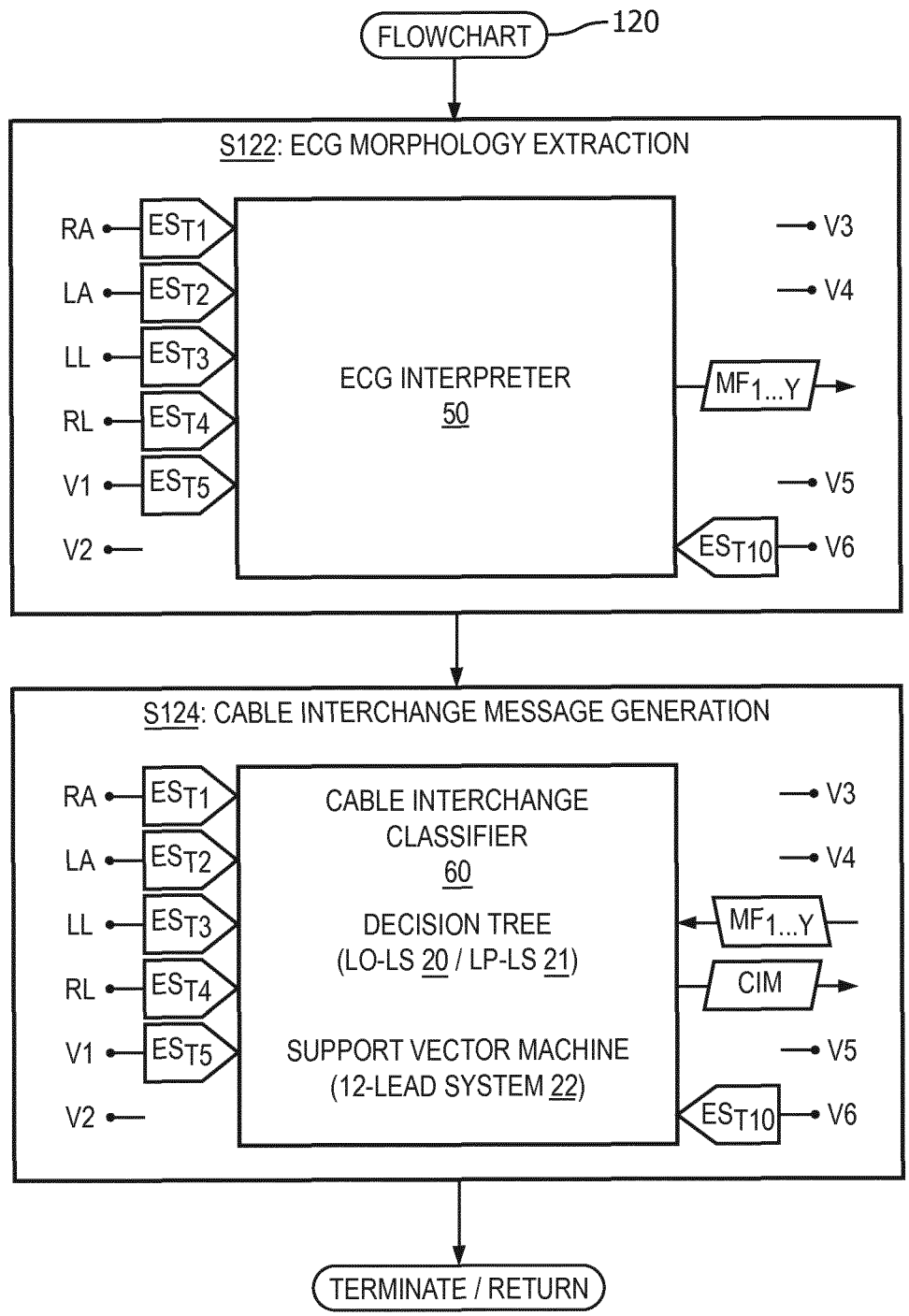
FIG. 6 illustrates a flowchart representative of a second exemplary embodiment of a morphology based detection/classification method in accordance with the inventive principles of the present invention.

Referring to FIG. 6, a flowchart 120 represents a cable interchange classification with P-wave and without P-wave for an identified connection to limited precordial-lead system 21.

A stage S122 of flowchart 120 encompasses ECG interpreter 50 extracting morphology features necessary for a cable interchange message generation during a stage S124 of flowchart 120. Specifically, stage S122 shows six (6) ECG signals $ES_{T1}$-$ES_{T5}$ and $ES_{T10}$ being communicated to ECG interpreter 50 via terminals T1-T5 and T10 of terminal configuration 41 whereby ECG interpreter 50 extracts up to a Y number of ECG morphology features MF, $Y \geq 1$.

For a normal P-wave, ECG interpreter 50 extracts and provides ECG morphology features MF including frontal axis of P-wave and QRS-wave, clockwise vector loop rotation direction of P-wave and QRS-wave, area of P-QRS-T-wave for two precordial leads, and amplitude of P-QRS-T-wave for two precordial leads to cable interchange classifier 60 for executing stage S124.

For an abnormal P-wave, ECG interpreter 50 extracts and provides ECG morphology features including frontal axis of QRS-wave, clockwise vector loop rotation direction of QRS-wave, amplitudes of R-wave for lead I and lead II, area of QRS-T-wave for two precordial leads, and amplitude of QRS-T-wave for two precordial leads to cable interchange classifier 60 for executing stage S124.

Note stage S122 shows "no cable interchange" between limited precordial-lead system 21 and terminal configuration 41. Nonetheless, those having ordinary skill in the art will appreciate the various cable interchanges that may occur for limited precordial-lead system 21.

Again, cable interchange classifier 60 incorporates a decision tree algorithm for limb only-lead system 20, a decision tree algorithm for limited precordial-lead system 21 and a support vector machine for standard 12-lead system 22. For flowchart 120, cable interchange classifier 60 executes the decision tree algorithm for limited precordial-lead system 21 for detecting and classifying any cable interchange between system 21 and terminal configuration 41. The decision tree is dependent upon the extracted features and utilizes predictive measurements of each extracted morphology feature should be chosen to balance sensitivity versus specificity.

Figure 7:
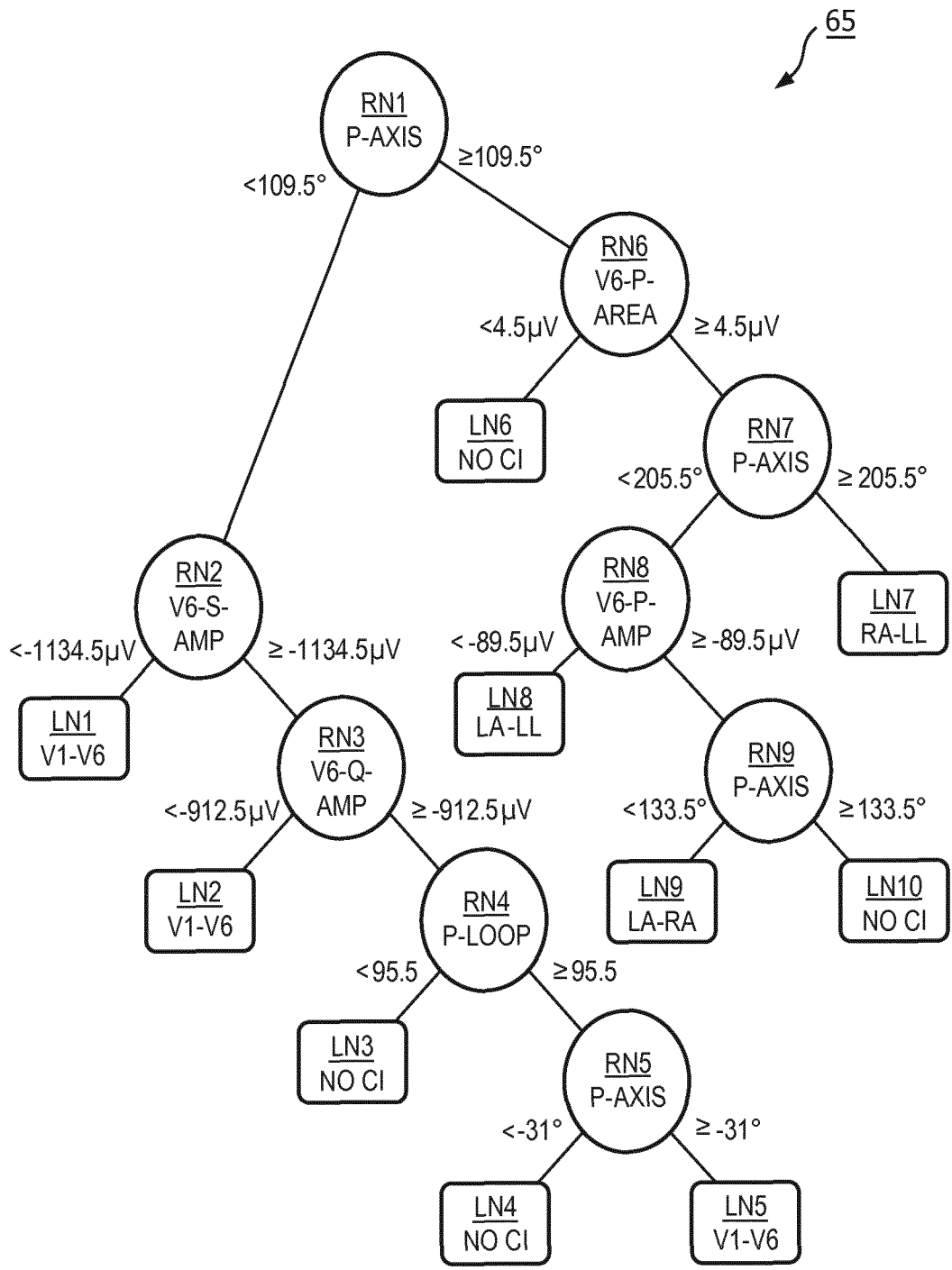
FIG. 7 illustrates a graphical diagram of a second exemplary embodiment of a decision tree in accordance with the inventive principles of the present invention.

Referring to FIG. 7, an exemplary decision tree 65 for a normal P-wave is shown. Decision tree 65 includes root node RN1-RN9 with each root node corresponding to a particular extracted ECG morphology feature. Decision tree 65 further includes leaf nodes LN1-LN10 with leaf nodes LN3, LN4, LN6 and LN10 corresponding to no cable interchange, and leaf nodes LN1, LN2, LN5 and LN7-LN9 corresponding to a particular cable interchange. The following Table 9 shows various message generations by cable interchange classifier 60 dependent upon specific measurements of extracted morphology features:

TABLE 9

|  | Measurement 1 | Measurement 2 | Measurement 3 |
|---|---|---|---|
| P-axis | 63° | 63° | 121° |
| P-loop [−100, 100] | 90 | 110 | 110 |
| Lead V6 P-area | 5.0 μv | 5.0 μv | 5.0 μv |
| Lead V6 P-amp | −71 μv | −71 μv | −71 μv |
| Lead V6 Q-amp | −874 μv | −874 μv | −874 μv |
| Lead V6 S-amp | −1034 μv | −1474 μv | −1474 μv |
| Cable Interchange Message | No CI | V1-V6 | LA-LL |

From the description of FIG. 7, those having ordinary skill in the art will appreciate, (1) how to re-balance sensitivity versus specificity of decision tree 65 as needed, and (2) how to generate a decision tree for an abnormal P-wave and alternative decision tree for normal P-wave, both including more or less or the same ECG morphology features as decision tree 65.

In practice, cable tree classifier 60 may utilize algorithms for limited precordial-lead system 21 other than a decision tree including, but not limited to, a linear regression, a logistic regression, a neural network, a naïve Bayes, and a discriminate analysis. Furthermore, any utilized algorithm may be used to solve a regression problem, which means in addition to detection of any cable interchange, each detection will be assigned a likelihood probability estimate.

Upon completion of stage S124, any cable interchange between limited precordial-lead system 21 and terminal configuration 41 has been accurately detected and classified, and classifier 60 provides a cable interchange message CIM.

Figure 8:
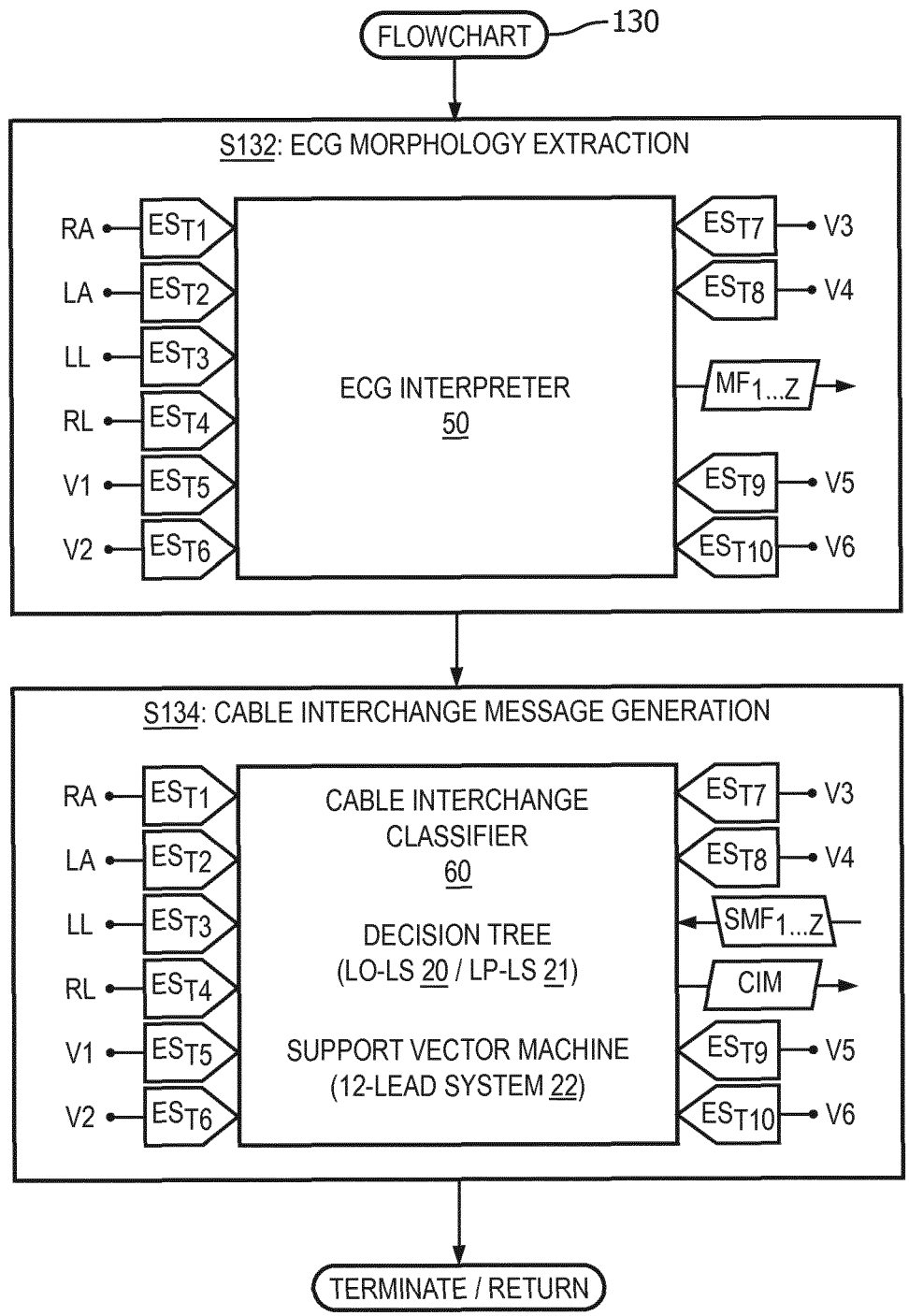
FIGS. 8 and 9 illustrate flowcharts representative of an exemplary embodiment of a morphology/redundancy based detection/classification method in accordance with the inventive principles of the present invention.

Referring to FIG. 8, a flowchart 130 represents a cable interchange classification with P-wave and without P-wave for an identified connection to standard 12-lead system 22.

A stage S132 of flowchart 130 encompasses ECG interpreter 50 extracting morphology features necessary for a cable interchange message generation during a stage S134 of flowchart 130. Specifically, stage S132 shows ten (10) ECG signals $ES_{T1}$-$ES_{T10}$ being communicated to ECG interpreter 50 via terminals T1-T10 of terminal configuration 41 whereby ECG interpreter 50 extracts up to a Z number of ECG morphology features MF, $Z \geq 1$.

For a normal P-wave, ECG interpreter 50 extracts and provides ECG morphology features MF including frontal axis of P-wave and QRS-wave and clockwise vector loop rotation direction of P-wave and QRS-wave to cable interchange classifier 60 for executing stage S134.

For an abnormal P-wave, ECG interpreter 50 extracts and provides ECG morphology features including ECG morphology features including frontal axis of QRS-wave, clockwise vector loop rotation direction of QRS-wave, and amplitudes of R-wave for lead I and lead II to cable interchange classifier 60 for executing stage S134.

Note stage S132 shows "no cable interchange" between standard 12-lead system 22 and terminal configuration 41. Nonetheless, those having ordinary skill in the art will appreciate the various cable interchanges that may occur for standard 12-lead system 22.

Again, cable interchange classifier 60 incorporates a decision tree algorithm for limb only-lead system 20, a decision tree algorithm for limited precordial-lead system 21 and a support vector machine for standard 12-lead system 22. For flowchart 130, cable interchange classifier 60 executes the support vector machine for standard 12-lead system 22 for detecting and classifying any cable interchange between system 22 and terminal configuration 41. The support vector machine processes the appropriate extracted ECG morphology features MF and redundancy features of the standard 12-lead system 22. In practice, any type of support vector machine may be utilized including, but not limited to, a multi-class linear support vector machine in the form of C-support vector classification.

Figure 9:
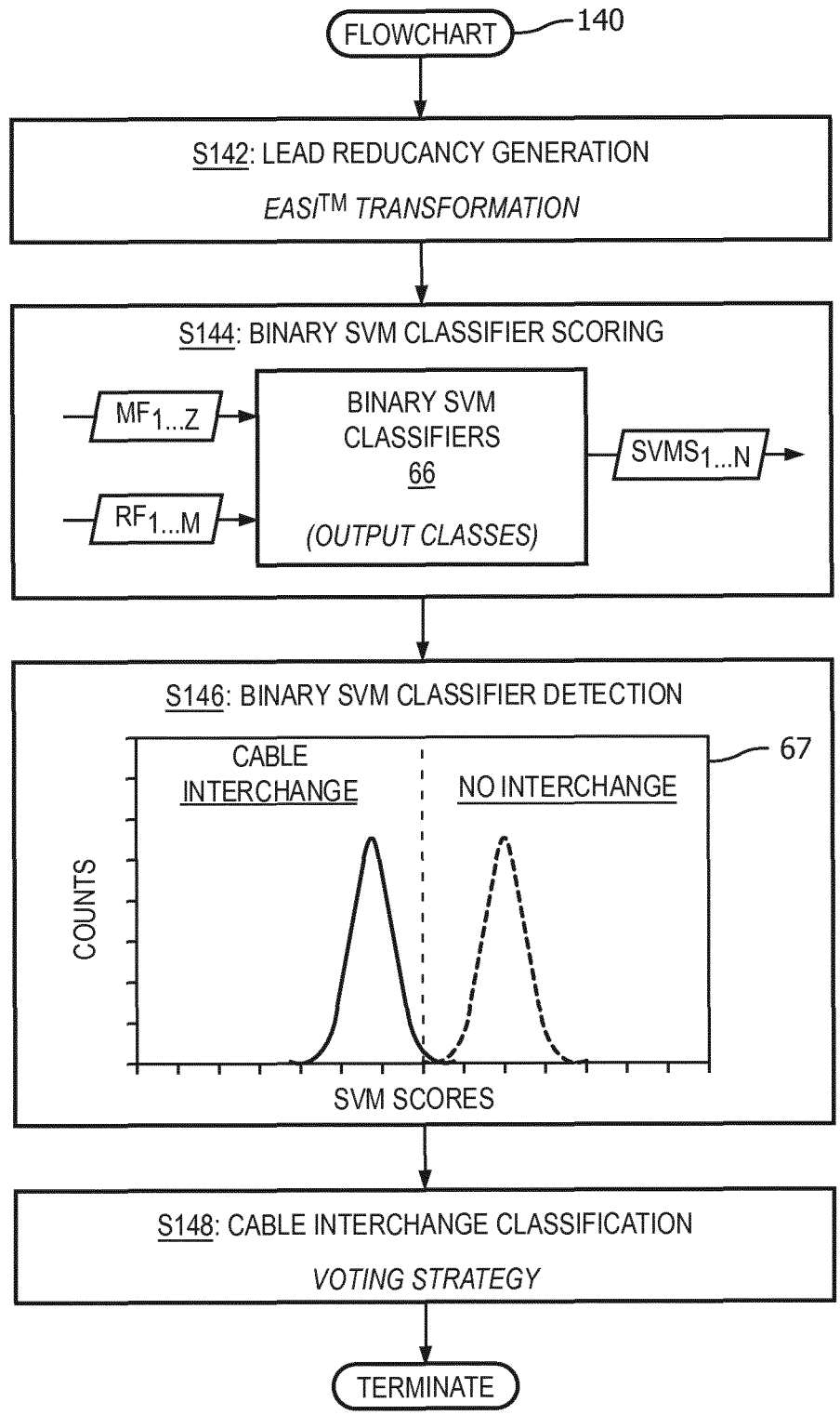

Referring to FIG. 9, a flowchart 140 represents a support vector machine method for stage S134 utilizing a multi-class linear support vector machine in the form of C-support vector classification.

A stage S142 of flowchart 140 encompasses classifier 60 generating a M number of redundancy features of standard 12-lead system 22, $M \geq 1$. In one embodiment of flowchart 140, the redundancy features are derived based on a known EASI™ transformation. In this context, redundancy means that many leads are highly correlated whereby each lead can be reconstructed from other leads with reasonable accuracy due to this redundant information. The transformation involves, for each ECG, after generating a separate ECG for all possible lead swaps, an inverse of EASI™ lead conversion matrix used to transform each swapped 12-lead ECG to the EASI™ lead system and then the EASI™ lead conversion matrix is applied to convert back to a 12-lead ECG. A lead by lead root mean square errors (RMSE) and correlation coefficient (CC) between swapped ECGs and the double EASI™-transformed ECGs are calculated over the entire QRS-T complex. The redundancy features are thus the averaged RMSE and averaged CC among all 12 leads for each lead swap.

In practice, a matrix transformation alternative to the EASI™ transformation may be utilized during stage S142.

A stage S144 of flowchart 140 encompasses an N number of output classes for each possible cable interchange, $N \geq 1$, and a N number of binary SVM classifiers 66 for every combination of output classes with a "no interchange" class. More particularly, a linear combination of extracted ECG morphology features MF and generated redundancy features RF are processed to generate a SVM score from each binary classifier.

A stage S146 of flowchart 140 encompasses a detection of any cable interchange by an application of each SVM score to a corresponding SVM score histogram 67 having a decision boundary between a "no interchange" class and a "cable interchange" class designed to reduce any false positive case through an unequal weighting of the C parameter in the SVM model.

A stage S148 of flowchart 40 encompasses a cable interchange classification based on a "one-against-one" approach whereby a final output class is chosen by comparing outputs from all binary classifiers using a voting strategy. The final output will be the class which has the most votes among all binary classifiers.

In a simple example, for ten (10) binary classifiers B1-B10 and three (3) possible output classes O1-O3, the following is the output of each binary classifiers:
1. B1->O1;
2. B2->O1;
3. B3->O2;
4. B4->O1;
5. B5->O1;
6. B6->O1;
7. B7->O2;
8. B8->O2;
9. B9->O3; and
10. B10->O3.

A voting tally of the outputs render output class O1 having five (5) votes, output class O2 having three (3) votes, and output class O3 having two (2) votes. So the final output would be output class O1.

From the description of FIG. 9, those having ordinary skill in the art will appreciate, implement different types of support vector machines of various classifications.

In practice, cable interchange classifier 60 may utilize algorithms for standard 12-lead system 22 other than a support vector machines including, but not limited to, a linear regression, a logistic regression, a neural network, a naïve Bayes, and a discriminate analysis. Furthermore, any utilized algorithm may be used to solve a regression problem, which means in addition to detection of any cable interchange, each detection will be assigned a likelihood probability estimate.

Upon completion of stage S146, any cable interchange between standard 12-lead system 22 and terminal configuration 41 has been accurately detected and classified, and classifier 60 provides a cable interchange message CIM.

Figure 10:
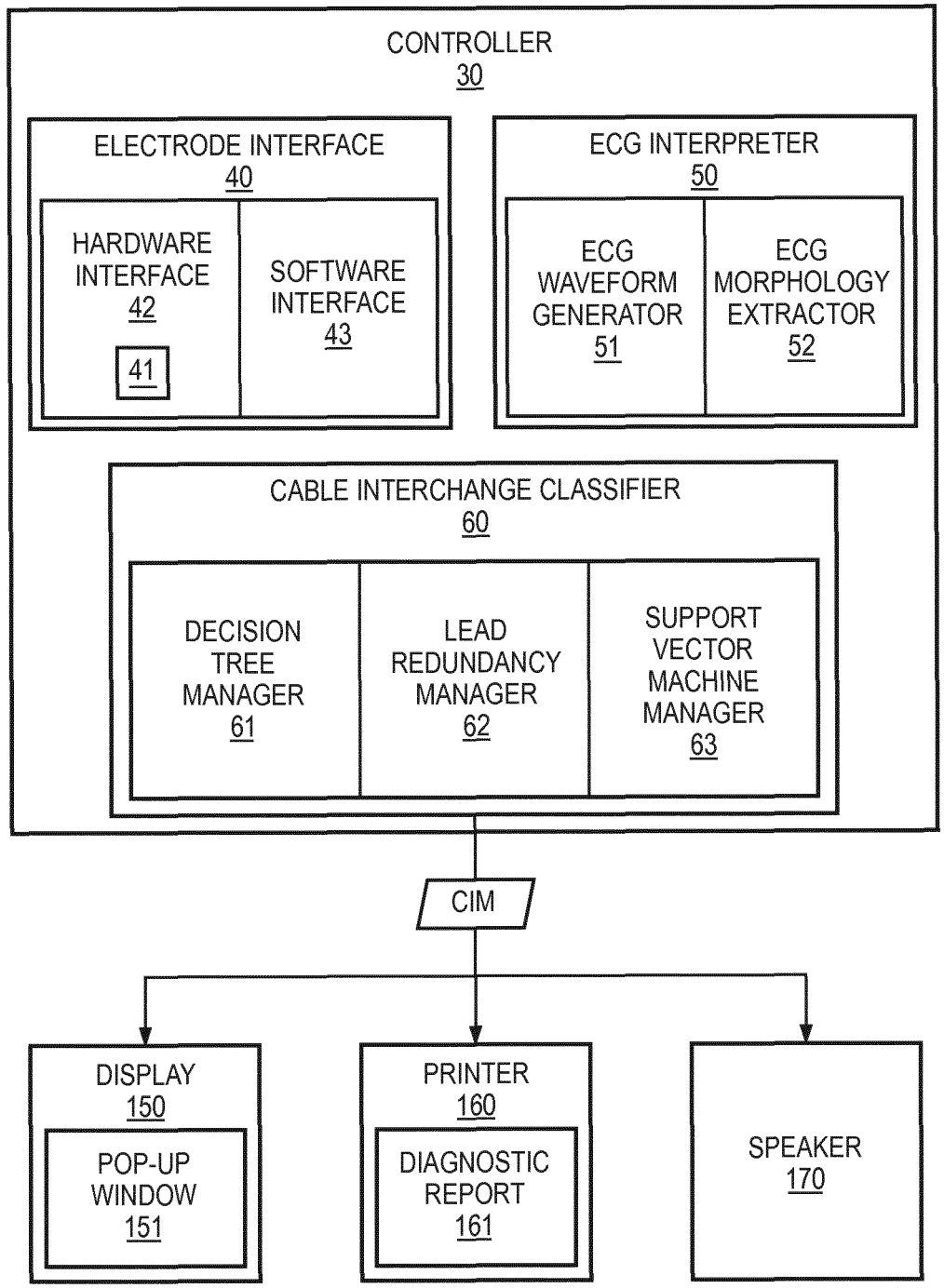
FIG. 10 illustrates a block diagram of an exemplary embodiment of an ECG controller in accordance with the inventive principles of the present invention.

Referring to FIG. 10, a more detailed exemplary embodiment of ECG controller 30 is shown for executing the preceding descriptions of various flowcharts as shown in FIGS. 2-9. For this embodiment, electrode interface 40 employs a hardware interface 41 inclusive of terminal configuration 41 (FIG. 1) and a software interface 42 for controlling of a transmission of ECG signals to ECG interpreter 50 and lead identification codewords to ECG interpreter 50 and cable interchange classifier 60. ECG interpreter 50 employs an ECG waveform generator 51 and an ECG morphology extractor 52. Cable interchange classifier 60 employs a decision tree manager 61, a lead redundancy manager 62 and a support vector machine manager 63.

Controller 30 may communicate a cable interchange message CIM to various devices including, but not limited to, a display 150, a printer 151 and a speaker 152. For example, cable interchange message CIM may be displayed by display 150 during a pre-recording screen of an ECG waveform. More particularly, in a clinical workflow, right after skin preparation, electrode placement, and device connection, a pop-up window 151 could be displayed if the algorithm detects any cable interchange.

Additionally, during a retrospective diagnosis, a message code could be displayed on a diagnostic report 161 generated by printer 160 and if possible interchanged leads could be swapped back to the correct position during post-recording analysis.

As previously stated herein, ECG controller 30 is for an ECG device by coupling, integration or otherwise any structural relationship between ECG controller 30 and the ECG device that facilitates the ECG controller communicating a message to or from the ECG device indicating an absence or a presence of a cable interchange between the ECG controller and an ECG lead system.

Figure 11A:
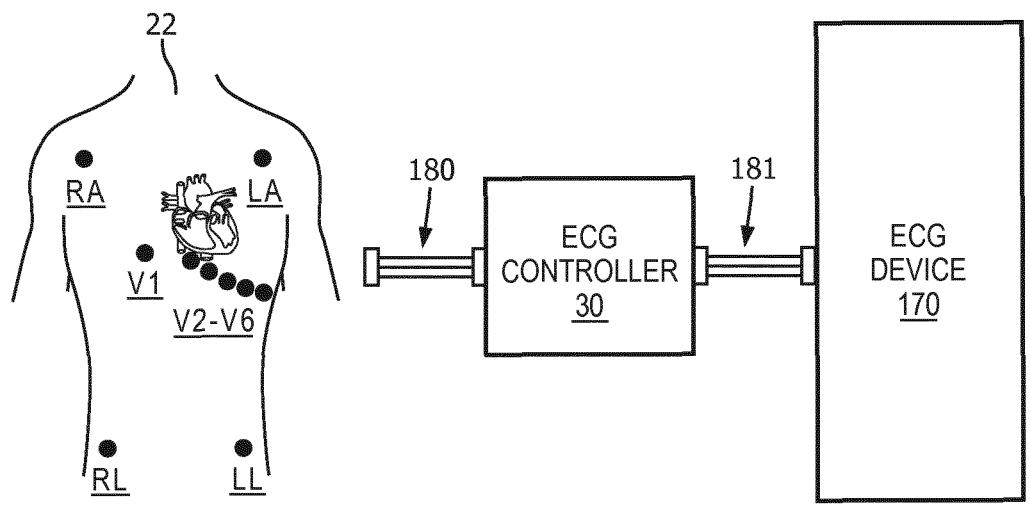
FIGS. 11A and 11B illustrate block diagrams of exemplary embodiments of an ECG controller/ECG device structural relationship in accordance with the inventive principles of the present invention.

For example, FIG. 11A shows a coupling of ECG controller 30 to an ECG device 170 via a cable connector 181 whereby ECG signals and a cable interchange message may be communicated to ECG device 170 upon a connection of ECG controller 30 to standard 12-lead system 22 (or other ECG lead system) via a cable connector 180.

Figure 11B:
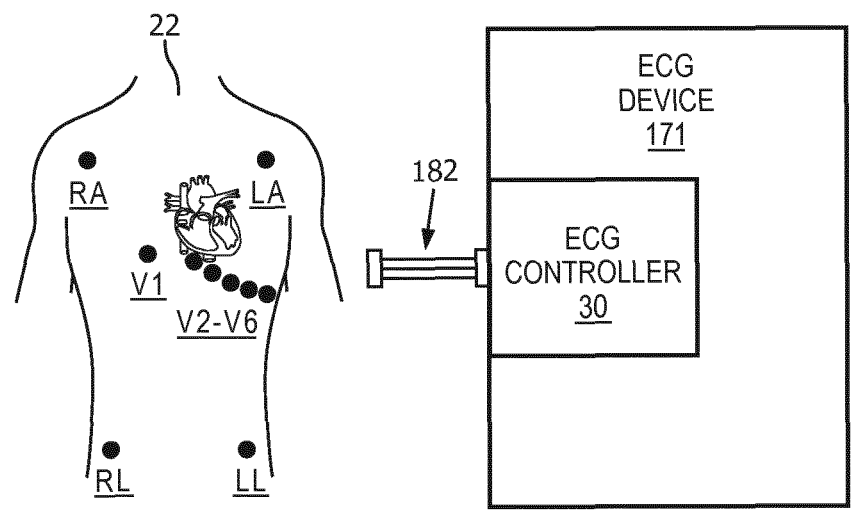

By further example, FIG. 11B shows an integration of ECG controller 30 into an ECG device 181 whereby ECG signals and a cable interchange message are communicated to additional components (not shown) of ECG device 181 as needed upon a connection of ECG controller 30 to standard 12-lead system 22 (or other ECG lead system) via a cable connector 180.

In practice, an ECG controller of the present invention may be designed for a specific ECG lead system only. For such designs, a cable interchange classifier may implement an ECG waveform morphology based detection and classification of the present invention and/or an ECG lead redundancy based detection (e.g., decision tree processing of morphology features) and classification of the present invention (e.g., SVM processing of morphology/redundancy features).

Referring to FIGS. 1-11, those having ordinary skill in the art will appreciate numerous benefits of the present invention including, but not limited to:

(1) facilitating a reduction in chances of ECG lead-wire misconnections by ECG technicians or nurses by generating an alert indicating cable interchange during initial ECG recordings for a wide range of ECG devices, and (2) facilitating a retrospective diagnosis by displaying an interchange message code on the diagnostic report and if possible swapping the interchanged leads back to the correct position to thereby impeded a generation erroneous diagnostic reports, false alarms, or preventing large waveform error when reconstructing ECGs from different lead systems.

Furthermore, as one having ordinary skill in the art will appreciate in view of the teachings provided herein, features, elements, components, etc. described in the present disclosure/specification and/or depicted in the FIGS. 1-11 may be implemented in various combinations of electronic components/circuitry, hardware, executable software and executable firmware, particularly as application modules of an ECG controller as described herein, and provide functions which may be combined in a single element or multiple elements. For example, the functions of the various features, elements, components, etc. shown/illustrated/depicted in the FIGS. 1-11 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk read only memory (CD-ROM), compact disk read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive system and method for automatic detection/classification of ECG cable interchange for difference ECG lead systems, (which embodiments are intended to be illustrative and not limiting), it is noted that modifications and variations can be made by persons having ordinary skill in the art in light of the teachings provided herein, including the FIGS. 1-11. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. An ECG controller for an ECG device, the ECG controller comprising:
    an electrode interface connectable to a base ECG lead system and connectable to a sub-base ECG lead system,
        wherein the electrode interface is configured to receive ECG signals from a connection to the base ECG lead system or the sub-base ECG lead system;
    an ECG interpreter,
        wherein, operable to the electrode interface receiving the ECG signals when the electrode interface is connected to one of the base ECG lead system or the sub-base ECG lead system, the ECG interpreter is configured to generate an ECG waveform from the ECG signals and
        further configured to extract at least one morphology feature of the ECG waveform; and
    a cable interchange classifier,
        wherein, operable to the ECG interpreter extracting the at least one morphology feature of the ECG waveform when the electrode interface is connected to the sub-base ECG lead system, the cable interchange classifier is configured to detect and classify any cable interchange between the electrode interface and the sub-base ECG lead system based on the at least one morphology feature of the ECG waveform, and
        wherein, operable to the ECG interpreter extracting the at least one morphology feature of the ECG waveform when the electrode interface is connected to the base ECG lead system, the cable interchange classifier is configured to generate at least one redundancy feature of the base ECG lead system from the ECG signals and further configured to detect and classify any cable interchange between the electrode interface and the base ECG lead system based on both the at least one morphology feature of the ECG waveform and the at least one redundancy feature of the base ECG lead system.

2. The ECG controller of claim 1, wherein the sub-base ECG lead system is a subset of the based ECG lead system.

3. The ECG controller of claim 1,
    wherein the base ECG lead system is a standard 12-lead system; and
    wherein the sub-base ECG lead system is one of a limb only-lead system and a limited precordial-lead system.

4. The ECG controller of claim 1, wherein responsive to a P-wave of the ECG waveform exhibiting normal characteristics, the ECG interpreter is configured to extract the at least one morphology feature of the ECG waveform including at least one of a frontal axis of a P-wave, a frontal axis of a QRS-wave, a clockwise vector loop rotation direction of the P-wave, a clockwise vector loop rotation direction of the QRS-wave, an area of a P-QRS-T wave, and an amplitude of the P-QRS-T wave.

5. The ECG controller of claim 1, wherein responsive to a P-wave of the ECG waveform exhibiting abnormal characteristics, the ECG interpreter is configured to extract the at least one morphology feature of the ECG waveform including a frontal axis of a QRS-wave, a clockwise vector loop rotation direction of the QRS-wave, amplitudes of the R-waves, an area of a QRS-T wave, and an amplitude of the QRS-T wave.

6. The ECG controller of claim 1, wherein the cable interchange classifier includes a decision tree for detecting and classifying any cable interchange between the electrode interface and the sub-base ECG lead system.

7. The ECG controller of claim 6,
    wherein the decision tree includes at least one root node corresponding to the at least one morphology feature of the ECG waveform; and
    wherein the decision tree further includes at least one leaf node corresponding to a cable interchange between the electrode interface and the sub-base ECG lead system.

8. The ECG controller of claim 1, wherein the cable interchange classifier is configured to derive the at least one redundancy feature of the base ECG lead system from a transformation matrix.

9. The ECG controller of claim 1,
    wherein the cable interchange classifier includes a support vector machine for detecting and classifying any cable interchange between the electrode interface and the base ECG lead system; and
    wherein the support vector machine includes a plurality of binary classifiers for generating interchange classification scores of the connection between the electrode interface and the base ECG lead system from linear combinations of the at least one morphology feature of the ECG waveform and the at least one redundancy feature of the base ECG lead system.

10. The ECG controller of claim 9, wherein the support vector machine includes a plurality of histograms for classifying each interchange classification score.

11. The ECG controller of claim 10, wherein the support vector machine is further configured to classify the connection between the electrode interface and the base ECG lead system from a voting strategy of the classifications of the interchange classification scores.

12. The ECG controller (30) of claim 1,
    wherein the sub-base ECG lead system includes a RA electrode, a LA electrode and a LL electrode; and
    wherein responsive to a detection by the cable interchange classifier of a cable interchange between the electrode interface and the sub-base ECG lead system, the cable interchange classifier is further configured to classify the cable interchange detection as one of a LA-RA interchange, a RA-LL interchange, a LA-LL interchange, a clockwise rotation rLAL interchange and a counter clockwise rotation rLAR interchange.

13. The ECG controller of claim 1,
wherein the sub-base ECG lead system includes a RA electrode, a LA electrode, a LL electrode, and two or more precordial electrodes; and
wherein responsive to a detection by the cable interchange classifier of a cable interchange between the electrode interface and the sub-base ECG lead system, the cable interchange classifier is further configured to classify the cable interchange detection as one of a LA-RA interchange, a RA-LL interchange, a LA-LL interchange, a clockwise rotation rLAL interchange, a counter clockwise rotation rLAR interchange and a precordial interchange.

14. The ECG controller of claim 13, wherein the pair of precordial electrodes are a V1 electrode and a V6 electrode.

15. The ECG controller of claim 1,
wherein the base ECG lead system includes a RA electrode, a LA electrode, a LL electrode, and precordial electrodes V1-V6; and
wherein responsive to a detection by the cable interchange classifier of a cable interchange between the electrode interface and the base ECG lead system, the cable interchange classifier is further configured to classify the cable interchange detection as one of a LA-RA interchange, a RA-LL interchange, a LA-LL interchange, a clockwise rotation rLAL interchange, a counter clockwise rotation rLAR interchange, and a precordial interchange.

16. A method of operating an ECG controller for an ECG device, the method comprising:
the ECG controller receiving ECG signals from one of a connection to a base ECG lead system or a connection to a sub-base ECG lead system;
the ECG controller generating an ECG waveform responsive to the ECG signals, and extracting a at least one morphology feature of the ECG waveform;
when the ECG controller is connected to the sub-base ECG lead system, the ECG controller detecting and classifying any cable interchange between the ECG controller and the sub-base ECG lead system from the at least one morphology feature of the ECG waveform;
when the ECG controller is connected to the base ECG lead system, the ECG controller generating at least one redundancy feature of the base ECG lead system from the ECG signals and
the ECG controller further detecting and classifying any cable interchange between the ECG controller and the base ECG lead system based on the at least one morphology feature of the ECG waveform and the at least one redundancy feature of the base ECG lead system.

17. The method of claim 16, further comprising:
the ECG controller ascertaining a connection to the base ECG lead system from a terminal configuration fully corresponding to the base ECG lead system or a connection to the sub-base ECG lead system from a terminal configuration partially corresponding to the sub-base ECG lead system.

18. The method of claim 16,
wherein the ECG controller implements a decision tree for detecting and classifying any cable interchange between the electrode interface and the sub-base ECG lead system;
wherein the decision tree includes at least one root node corresponding to the at least one morphology feature of the ECG waveform; and
wherein the decision tree further includes at least one leaf node corresponding to a cable interchange between the electrode interface and the sub-base ECG lead system.

19. The method of claim 16, wherein the ECG controller derives the at least one redundancy feature of the base ECG lead system from a transformation matrix.

20. The method of claim 16,
wherein the ECG controller executes a support vector machine for detecting and classifying any cable interchange between the electrode interface and the base ECG lead system; and
wherein the support vector machine includes a plurality of binary classifiers for generating interchange classification scores of the connection between the electrode interface and the base ECG lead system from linear combinations of the at least one morphology feature of the ECG waveform and the at least one redundancy feature of the base ECG lead system.

* * * * *